US005667785A

United States Patent [19]

Gerber et al.

[11] Patent Number: 5,667,785

[45] Date of Patent: Sep. 16, 1997

[54] VACCINE FOR PROTECTION OF CATS AGAINST FELINE INFECTIOUS PERITONITIS

[75] Inventors: Jay Dean Gerber; Jerald Dee Ingersoll, both of Lincoln, Nebr.

[73] Assignee: Pfizer Inc., New York, N.Y.

[21] Appl. No.: 280,405

[22] Filed: Jul. 26, 1994

Related U.S. Application Data

[63] Continuation of Ser. No. 84,778, Jun. 28, 1993, abandoned, which is a continuation of Ser. No. 852,880, Mar. 17, 1992, abandoned, which is a continuation-in-part of Ser. No. 428,796, Oct. 30, 1989, abandoned, which is a continuation-in-part of Ser. No. 758,540, Sep. 9, 1991, abandoned, which is a continuation of Ser. No. 103,144, Oct. 1, 1987, abandoned.

[51] Int. Cl.$^6$ .......... A61K 39/215; A61K 39/38; C12N 7/00; C12N 7/08

[52] U.S. Cl. .......... 424/221.1; 424/204.1; 424/184.1; 435/236; 435/237; 435/235.1; 435/239

[58] Field of Search .......... 424/184.1, 204.1, 424/221.1, 239; 435/236, 237, 235.1

[56] References Cited

U.S. PATENT DOCUMENTS

| | | | |
|---|---|---|---|
| 4,195,130 | 3/1980 | Hoshino et al. | 435/235 |
| 4,303,644 | 12/1981 | Davis et al. | 424/89 |
| 4,571,386 | 2/1986 | Fishman et al. | 435/235 |

FOREIGN PATENT DOCUMENTS

| | | | |
|---|---|---|---|
| 0011864 | 11/1979 | European Pat. Off. | C12N 7/00 |
| 0027347 | 4/1981 | European Pat. Off. | A61K 39/215 |
| 138242 | 8/1984 | European Pat. Off. | C12N 15/00 |
| 0310362 | 5/1989 | European Pat. Off. | A61K 39/12 |
| 8704624 | 8/1987 | WIPO | C12N 7/08 |

OTHER PUBLICATIONS

Platkin et al. 1988. Vaccines pp. 568–575; New Technologies for Making Vaccines.

Pedersen et al. 1985. Viral Diseases of Small Animals: Thirty Fourth Annual Symposium 7:1001.

Lutz, et al., J. Small Anim. Pract. 27:108(1986).

Pedersen, et al., Viral Diseases of Small Animals: Thirt–Fourth Annual Symposium 7;1001(1985).

Pedersen, et al., Am. J. Vet Res. 44:229*1983).

Scott, et al., "Attenuation of Feline Infectious Peritonitis Virus." Sixty–Ninth Conference of Research Workers in Animal Disease, Nov. 14–15, 1988.

*Primary Examiner*—N. M. Minnifield
*Attorney, Agent, or Firm*—Peter C. Richardson; Paul H. Ginsburg; Alan L. Koller

[57] ABSTRACT

This invention relates to a temperature-sensitive (ts) feline infectious peritonitis (FIP) virus, which is characterized by substantially reduced growth at 39° C. as compared with its growth at 31° C. Also included in this invention is the use of the ts-FIP virus for oral or intranasal administration to cats as a vaccine to induce immunity against FIP.

22 Claims, No Drawings

VACCINE FOR PROTECTION OF CATS AGAINST FELINE INFECTIOUS PERITONITIS

This is a continuation of application Ser. No. 08/084,778, filed Jun. 28, 1993 now abandoned, which is continuation of application Ser. No. 07/852,880 filed Mar. 17, 1992 now abandoned, which is a continuation in part of application Ser. No. 07/428,796 filed Oct. 30, 1989 now abandoned, which is a continuation in part of application Ser. No. 07/758,540 filed Sep. 9, 1991 now abandoned, which is a continuation of application Ser. No. 07/103,144 filed Oct. 1, 1987 now abandoned.

FIELD OF INVENTION

This invention relates to a method of administering a vaccine useful for the immunization of cats against the feline infectious peritonitis (FIP) virus.

BACKGROUND OF THE INVENTION

Feline infectious peritonitis (FIP) is a disease of both domestic and wild cats. The virus affects most of the internal organs of the animal and is almost always fatal. The virus is highly contagious, affecting kittens as well as adult cats.

The FIP virus was identified as a coronavirus by Horzinek and Osterhaus, *Arch. Virol.* 59:1(1979). FIP virus is related to transmissible gastroenteritis virus (TGEV) of pigs, enteric coronavirus of dogs and a respiratory coronavirus of man. There is also a feline enteric coronavirus (FECV) that replicates mainly in the intestine and causes only a mild diarrheal disease. Lutz, et al., *J. Small Animal Pract.* 27:108 (1986).

Although it is known that FIP is caused by a coronavirus, the manner in which the infection is transmitted among cats and its pathogenesis are still poorly understood. The pathogenesis of the disease is very complex and studies indicate that host, viral and environmental factors play a role in the form and progression of the disease. Pedersen, et al., *34th Annual Symposium, Viral Diseases of Small Animals* 7:1001 (1985).

FIP can occur in two different forms: the wet or effusive form characterized by a fibrinous peritoneal exudate and the dry or parenchymatous form which is characterized by granulomatous inflammation of different organs and little or no exudate. Lutz, et al., supra.

Because there are other coronavirus infections of cats, for example, FECV, which are antigenically related to FIP virus, the pathogenesis of FIP has been difficult to characterize. As a result, serological tests for diagnosis of the disease have lacked specificity and have confused the interpretation of earlier studies. Pederson, *Feline Practice* 13:13(1983).

Until recently, protective active immunization against FIP was not possible. On the contrary, vaccinated cats were more susceptible to disease. Pedersen, et al., *Am. J. Vet. Res.* 44:229(1983); Weiss, et al., *Comp. Immun. Microbiol. Infect. Dis.* 4:175(1981); Weiss, et al., *Am. J. Vet. Res.* 41:663(1980).

Cats are infected by the oronasal route. FIP virus multiplies in epithelial cells of the upper respiratory tract and intestine. Clinically apparent FIP occurs after the virus crosses the mucosal barrier and causes an immune mediated disease. Lutz, et al., supra., Weiss, et al., *Am. J. Vet. Res.* 42:382(1981).

Stimulation of a nasal mucosal immune response is best done by intranasal administration of a vaccine. Bienenstock, et al., *Immunology* 41:249(1980); Murray, *The Veterinary Record Nov. 10th*:500(1973). Mucosal B-lymphocytes, stimulated to secrete anti-FIP virus IgA antibody, will also migrate to the gut mucosa and also confer local gut immunity. Murray, supra.

This invention is of a method for protecting feline animals against infection by FIP Virus which comprises intranasally administering an effective amount of a FIP Virus vaccine. This invention is also a FIP Virus vaccine comprising a temperature-sensitive (ts) FIP Virus. These and related aspects of the invention are fully described hereinbelow.

In a related aspect, this invention is a device for intranasally administering to a feline animal a non-pathogenic FIP Virus.

DETAILED DESCRIPTION OF THE INVENTION

Intranasal administration of a FIP Virus vaccine provides a surprisingly and unexpectedly improved immunogenic response. The vaccines which are useful in this aspect of the invention typically comprise an amount of a non-pathogenic FIP Virus (i.e., a strain of FIP virus which does not typically cause disease in healthy cats) which is effective to induce a protective immune response to infection by FIP. Such non-pathogenic FIP Virus typically is attenuated by multiple passage in cell culture or is modified by mutagenesis. For example, Fishman et al., U.S. Pat. No. 4,571,386, disclose an attenuated FIP Virus which, according to the patentee, does not cause disease; Scott et al., 69th Conference of Research Workers in Animal Disease, 1988 (Abstract), disclose attenuation of FIP Virus by multiple passage. Baldwin, et al., Patent Cooperation Treaty (PCT) application WO 87/04624, describe preparation of an attennuated FIP Virus vaccine; Pedersen, et al., *Viral Diseases of Small Animals: Thirty-fourth Annual Symposium* 7:1001(1985)., set forth the parameters believed necessary in order to develop a safe and efficacious vaccine against FIP virus; Pedersen, et al., *Am J. Vet Res.* 44:229(1983) describe results obtained when cat populations were administered a vaccine comprising an avirulent modified live FIP virus. All of these references are herein incorporated by reference as though fully set forth. Any effective FIP vaccine can, in accordance with this invention, be administered intranasally, including, for example, subunit vaccines and heterotypic vaccines, in addition to inactivated, modified or attenuated FIP Virus.

An effective FIP vaccine should stimulate a strong mucosal immune response in order to prevent an infection from crossing the mucosal barrier and a cell-mediated immune (CMI) response that will immediately halt the spread of virus if it crosses the mucosa. In the preferred embodiment of the invention, a temperature sensitive FIP (ts-FIP) virus is administered intranasally. When it is given intranasally, the ts-FIP virus, because of its ability to grow at temperatures present in the nasopharynx region, readily propagates and stimulates a CMI response and local immune response. In addition, ts-FIP virus stimulates a CMI response to FIP virus following challenge which is not detected in cats vaccinated systemically or in cats infected with virulent FIP virus.

The FIP virus used to prepare the preferred vaccine of this invention is isolated from organs or tissues, preferably the liver, of animals infected with the virus. The organs or tissues are ground up and given orally to the experimental animals, preferably to specific pathogen free (SPF) cats.

After several in vivo passages of infected organs, preferably five in vivo passages of infected spleens or livers, the FIP virus is isolated. The FIP virus is isolated from the infected organs using standard procedures known in the art and cocultured with feline cells. The FIP virus grows readily with feline cells from any source, for example, spleen, mesenteric lymph node, endothelial cells or embryonic cell cultures such as taught by Davis, U.S. Pat. No. 4,303,644 and Fishman, et al., U.S. Pat. No. 4,571,386. In the preferred embodiment of the invention, the FIP virus is isolated from the cells of the diseased tissue and cocultured with feline kidney cells.

The virus extracted from the diseased tissues is cocultured with feline cells in order to adapt the virus to in vitro propagation. In vitro propagation is demonstrated by formation of multinucleated, syncytial cells along with other known cytopathic effects ("cpe") typical of coronaviruses. The virus is passaged until attenuation and then is mutated in order to be made temperature sensitive. In the art, attenuated is defined to mean the virus has been modified in such a manner as to be no longer capable of causing disease. Finally, the attenuated, temperature sensitive virus is administered to cats through either an oral or intranasal route.

In a preferred embodiment, the FIP virus is attenuated by high passage, for example, at least 60 passages, preferably 95–100 passages, in feline kidney cells. For development of a temperature sensitive FIP virus, an aliquot of culture fluid, at a high passage number is exposed to a mutagenic agent, e.g., chemical or irradiation; preferably ultraviolet irradiation, until virus titer following propagation at about 31° C. is at least $1\times10^2$ $TCID_{50}$, preferably about $1\times10^5$ $TCID_{50}$, greater than at 39° C. ($TCID_{50}$ is the tissue culture infective dose which produces a cytopathic effect; in 50% of the cultured cells exposed to the virus.)

To obtain optimum virus viability, the viral fluids are collected every 5 minutes and stored at −70° C. Ten-fold serial dilutions ($10^0$ to $10^{-7}$) of each 5 minute sample are tested for virus viability on confluent feline kidney cell monolayers. The optimal sample, preferably the 5 minute sample, is selected and propagated at 31° C. at various dilutions. Viral fluids from wells containing single plaques are collected.

Table 1 shows the effect of ultraviolet-irradiation of a virulent strain of FIP virus (DF2-FIP virus) at 31° C. FIP virus was completely inactivated after exposure to ultraviolet light for 10 minutes.

TABLE 1

Effect of Time of UV-Irradiation on the Virus Titer

| | Number of Virus Infected Wells/Dilution | | | | | | | | $TCID_{50}$ |
|---|---|---|---|---|---|---|---|---|---|
| Sample | $10^0$ | $10^{-1}$ | $10^{-2}$ | $10^{-3}$ | $10^{-4}$ | $10^{-5}$ | $10^{-6}$ | $10^{-7}$ | Titer |
| Pre-UV | 4/4[a] | 4/4 | 4/4 | 4/4 | 4/4 | 4/4 | 4/4 | 1/4 | $\geq 10^{6.67}$ |
| 5 minute | 4/4 | 3/4 | 0/4 | 0/4 | 0/4 | 0/4 | 0/4 | 0/4 | $10^{1.33}$ |
| 10 minute | 0/4 | 0/4 | 0/4 | 0/4 | | | | | 0 |
| 15 minute | 0/4 | 0/4 | 0/4 | 0/4 | | | | | 0 |

[a]Number of FIPV infected wells/total number of wells.

FIP virus fluids at a 1:16 dilution exposed to ultraviolet-irradiation for 5 minutes contained viral plaques. Single plaques are propagated in a majority of the wells.

Individual single plaques are titrated in ten fold dilutions ($10^{-3}$ to $10^{-8}$) in 24 well plates at 31°, 37° and 39° C. (Table 2).

TABLE 2

Titration of UV-Irradiated Viral Plaques at 31°, 37°, and 39° C.

| Plaque | Temperature | Number of Virus-Infected Wells/Dilution | | | | | | $TCID_{50}$ |
|---|---|---|---|---|---|---|---|---|
| No. | °C. | $10^{-3}$ | $10^{-4}$ | $10^{-5}$ | $10^{-6}$ | $10^{-7}$ | $10^{-8}$ | Titer |
| 1 | 31 | 4/4 | 4/4 | 4/4 | 4/4 | 2/4 | 0/4 | 7.00 |
| | 37 | 4/4 | 4/4 | 4/4 | 4/4 | 0/4 | 0/4 | 6.50 |
| | 39 | 4/4 | 4/4 | 4/4 | 2/4 | 1/4 | 0/4 | 6.23 |
| 2 | 31 | 4/4 | 4/4 | 4/4 | 4/4 | 4/4 | 0/4 | 7.50 |
| | 37 | 4/4 | 4/4 | 4/4 | 4/4 | 3/4 | 0/4 | 7.33 |
| | 39 | 4/4 | 4/4 | 4/4 | 2/4 | 0/4 | 0/4 | 6.00 |
| 3 | 31 | 4/4 | 4/4 | 4/4 | 4/4 | 4/4 | 1/4 | 7.67 |
| | 37 | 4/4 | 4/4 | 4/4 | 4/4 | 1/4 | 1/4 | 6.88 |
| | 39 | 4/4 | 4/4 | 4/4 | 3/4 | 0/4 | 0/4 | 6.33 |
| 4 | 31 | 4/4 | 4/4 | 4/4 | 4/4 | 4/4 | 0/4 | 7.50 |
| | 37 | 4/4 | 4/4 | 4/4 | 3/4 | 1/4 | 0/4 | 6.50 |
| | 39 | 0/4[a] | 0/4[b] | 0/4 | 0/4 | 0/4 | 0/4 | ≦3.50 |

[a]Four wells displayed scarring, or indications of early infection healed over.
[b]Three wells displayed scarring, or indication of early infection healed over.

The optimum conditions for propagating the virus are based on its ability to propagate at permissive temperatures. At 39° C. the $TCID_{50}$ is at least about $1\times10^2$ units lower than the $TCID_{50}$ at 31° C. and is preferably at least about $1\times10^5$ units lower.

TABLE 3

A Comparison of Viral Propagation for 5 in vitro Passages of a Temperature-Sensitive Plaque-Isolated FIPV at 31° C. and 39° C.

| | | Number of Virus-Infected Wells/Dilution | | | | | | | | $TCID_{50}$ |
|---|---|---|---|---|---|---|---|---|---|---|
| Passage | Temperature | $10^{-1}$ | $10^{-2}$ | $10^{-3}$ | $10^{-4}$ | $10^{-5}$ | $10^{-6}$ | $10^{-7}$ | $10^{-8}$ | Titer |
| 1 | 31° | 4/4[a] | 4/4 | 4/4 | 4/4 | 4/4 | 3/4 | 0/4 | 0/4 | 6.33 |
| | 39° | 4/4 | 0/4 | 0/4 | 0/4 | 0/4 | 0/4 | 0/4 | 0/4 | 1.50 |
| 2 | 31° | 4/4 | 4/4 | 4/4 | 4/4 | 4/4 | 1/4 | 0/4 | 0/4 | 5.67 |
| | 39° | 4/4 | 0/4 | 0/4 | 0/4 | 0/4 | 0/4 | 0/4 | 0/4 | 1.50 |
| 3 | 31° | 4/4 | 4/4 | 4/4 | 4/4 | 3/4 | 1/4 | 0/4 | 0/4 | 5.50 |
| | 39° | 0/4 | 0/4 | 0/4 | 0/4 | 0/4 | 0/4 | 0/4 | 0/4 | ≦1.50 |
| 4 | 31° | 4/4 | 4/4 | 4/4 | 4/4 | 4/4 | 1/4 | 0/4 | 0/4 | 5.67 |
| | 39° | 0/4 | 0/4 | 0/4 | 0/4 | 0/4 | 0/4 | 0/4 | 0/4 | ≦1.50 |
| 5 | 31° | 4/4 | 4/4 | 4/4 | 4/4 | 4/4 | 2/4 | 0/4 | 0/4 | 6.00 |
| | 39° | 0/4 | 0/4 | 0/4 | 0/4 | 0/4 | 0/4 | 0/4 | 0/4 | ≦1.50 |

[a]Number of FIPV infected wells/Total number of wells.

The attenuated temperature sensitive FIP virus of the present invention can be administered to felines to protect the animals from FIP virus. A dosage is selected which is safe, i.e., does not cause serious side effects and is effective, i.e., induces a protective cellular and local immune response following administration. The dosage which is effective when administered intranasally is approximately the same as when administered orally or by injection. A typical dose of FIP virus is $10^2$ to $10^7$ $TCID_{50}$ in a volume of about 0–25 to 1 ml.

The dose may be administered as a single dose or as several dilute doses over a period of time. A single dose of $10^{5.5}$ $TCID_{50}$ virus in 0.5 ml of carrier is preferred with one half of 0.5 ml (0.25 ml) administered by, for example, spray or squeeze bottle or by dropper to each nostril of the animal. A suitable spray bottle can be of the pump type or of the compressed gas type. Experimental results indicate an effective vaccinal dose can be administered as a single dose, two doses being preferred.

Typically, a device for intranasal administration of a FIP vaccine to a feline animal comprises a squeeze or spray bottle or a dropper. In a preferred device, the invention is a dropper. In another embodiment, the invention is a kit comprising two components one of which is container having an FIP vaccine in lyophilized form and the second of which is a dropper having a diluent for reconstitution. The components are used by squeezing the contents of the dropper into the container of lyophilized vaccine, shaking or stirring the vaccine to effect reconstitution, drawing up the reconstituted vaccine back into the dropper, and then, applying the contents of the dropper to the nostrils of a cat.

The FIP vaccine can be administered directly, i.e., the virus is grown in cell culture fluid and the culture fluid is then used as the carrier for administration. The culture fluid can be diluted or concentrated by standard techniques to achieve the desired concentration of attenuated ts-FIP virus. Alternatively, a pharmaceutically acceptable preparation of ts-FIP virus can be achieved by extracting the attenuated, temperature sensitive virus from the cell culture by, for example, sucrose density centrifugation separation techniques and mixing with a suitable carrier, for example, water, saline, cholera toxoid, or ovalbumin or with an adjuvant, e.g., Quil A, alhydrogel or an oil emulsion.

In the preferred embodiment, the virus is administered in the culture fluid and aliquots of single dose amounts are prepared. The avirulent, ts-FIP virus may also be lyophilized in single dosage amounts and stored until use. When stored as a lyophilized powder, the vaccine is reconstituted prior to administration in water, saline, culture fluid or other appropriate carriers suitable for direct intranasal administration in cats.

Measurements of antibody response are determined using standard methods, such as enzyme linked immunosorbent assay (ELISA) and a serum virus neutralization (VN) test, and are conducted on blood samples from individual animals. Measurements are made optimally on samples following vaccination and challenge. The lymphocyte blastogenesis procedure as described by Pedersen, et al., *The Compendium on Continuing Education* 7:1001(1985) is used to show a cell-mediated (lymphocyte) response following vaccination and challenge.

A further aspect of this invention is the preparation and use of combination vaccines consisting of vaccinal amounts of the ts-FIP virus and one or more known feline viruses. For example, combination vaccines can be prepared for oral or intranasal administration consisting of the ts-FIP virus component and one or more feline viruses known to be causative of respiratory infections, e.g., calicivirus, feline herpes (rhinotracheitis) virus.

Other combination vaccines capable of inducing immunity in cats to infection by FIP virus and one or more other pathogenic organisms or viruses can also be prepared utilizing the ts-FIP virus component and other non-respiratory related virus components or pathogenic organisms, e.g., feline distemper (panleukopenia), chlamydia, feline leukemia.

Subunit vaccines can also be prepared. The ts-FIP virus can be combined with subunits of killed or attenuated pathogens, for example, subunit components of feline distemper virus, calicivirus, feline herpes virus or the like for parenteral or intranasal administration. The ts-FIP virus may also be combined with feline leukemia virus vaccine for parenteral administration.

The preparation and use of such combination vaccines is carried out according to procedures as described herein or within the knowledge of those skilled in the art of vaccine production and use.

EXAMPLES

The examples which follow are illustrative and are not limiting of the invention.

EXAMPLE 1

Efficacy Test 1

Fourteen SPF male cats (26 months of age) from Liberty Labs (Liberty, N.J.) were used in the first vaccination-challenge test. Vaccinated cats were kept in one isolation room, nonvaccinated cats in another.

Ten cats were vaccinated 3 times intranasally (IN) 3 weeks apart with ts-FIP virus. Five cats were vaccinated with ts-FIP virus with a virus titer of $10^{5.5}$ $TCID_{50}$/ml at 31° C. and five with ts-FIP virus with a $10^{3.5}$ $TCID_{50}$/ml at 31° C. The ten vaccinates and four controls were challenged orally with 1 ml of a 1:600 dilution of virulent FIP virus (FIP virus-DF2, passage 10, challenge titer=$10^{2.68}$ $TCID_{50}$/ml) two weeks later.

The IgG serologic response to FIP virus was determined by ELISA, Osterhaus, et al., *Veterinary Quarterly* 1:59 (1979). The VII titers (Pedersen, et al., *Am. J. Vet. Res.* 44:229(1983)) were also determined.

The IgG ELISA titers of ts-FIP virus vaccinates is shown in Table 4. Pre-vaccination titers of vaccinated cats were on the day they were removed from isolation cages. Control cats had pre-vaccination ELISA titers 15 days after being removed from isolation cages. The response of control cats to FIP virus is due to antibodies to cross-reacting feline enteric coronavirus (FECV) endemic in the SPF cat colony used for the experiments. As a result, the IgG response of vaccinated cats is due to FECV as well as to the vaccine virus.

Virus neutralizing titers, which in contrast to IgG ELISA titers, were negative prior to vaccination, (Table 5) increased after each vaccination. Serum was not collected postchallenge for antibody titration. Pre-exposure of vaccinated and control cats with FECV had little if any effect on the challenge since both groups had developed a cross-reactive antibody response to FIP virus. Three of four nonvaccinated control cats developed FIP and died. The fourth cat, LK2, had a clinical score of 13 (the higher the number, the more severe the symptom, with death scored as 50), three times as high as any of the nine protected vaccinates.

EXAMPLE 2

Efficacy Test 2

Twelve coronavirus negative SPF male cats (12 months of age) from Liberty Labs were used in a second vaccination-challenge test. All cats were placed in isolation cages (three cats per cage).

Six cats were vaccinated three times IN three weeks apart with ts-FIP virus. Three cats were vaccinated two times IN with ts-FIP virus and once orally. The ts-FIP virus titer was $10^{5.5}TCID_{50}$/ml. The three non-vaccinated control cats were kept in a cage separate from vaccinates.

The nine vaccinates and three controls were challenged orally with 1 ml. of a 1:600 dilution of virulent FIP virus (FIP virus-DF2, passage 10, challenge titer=$10^{2.15}$ $TCID_{50}$/ml).

The serum IgG anti-FIP virus antibody response of ts-FIP virus vaccinated and non-vaccinated cats by ELISA is shown in Table 6. The greatest increase in IgG antibody titer was seen following the first and second vaccinations. No increase in titer occurred in those cats vaccinated IN a third time, confirming that one or at most two doses was sufficient to elicit protection. IgG antibody titers increased sharply following challenge. The virus neutralizing antibody titers increased following each of the three vaccinations and challenge (Table 7).

Two of three non-vaccinated control cats developed FIP and died. All of the vaccinated cats survived. Two vaccinated cats, SN1 and SY1 had temporary blood dyscrasias, primarily Doehle Bodies, low packed cell volume and an elevated body temperature. They did not, however, show any signs of icterus which is a good indicator of impending death.

EXAMPLE 3

Efficacy Test 3

Eighteen coronavirus negative SPF male cats (12 months of age) from Liberty Labs were used. All cats were placed in isolation cages (two cats per cage).

Six cats were vaccinated twice IN three weeks apart with ts-FIP virus. Six cats were vaccinated once IN. The ts-FIP virus titer was $10^{5.5}TCID_{50}$/ml. Six additional cats were vaccinated subcutaneously (SC) with Concanavalin A (Con A) adjuvanted ts-FIP virus and kept in separate cages from the IN vaccinates. Six non-vaccinated control cats were kept in cages separate from the vaccinates, The twelve vaccinates and six controls were challenged orally three weeks later with 1 ml of a 1:600 dilution of virulent FIP virus (FIP virus-DF2 passage 10, challenge titer=$10^{2.61}$ $TCID_{50}$/ml).

Table 8 shows the ELISA IgG titers of IN and subcutaneous ts-FIP virus vaccinated and non-vaccinated cats. Cats vaccinated twice IN and even once IN had higher mean titers than cats vaccinated SC at the time of challenge. Cats receiving two IN doses of ts-FIP virus vaccine also had higher VN titers than cats receiving a single IN dose prior to challenge (Table 9). Even one dose of ts-FIP virus administered IN stimulated higher VN titers than two doses given SC.

Peripheral blood lymphocytes from five of six cats vaccinated twice IN responded to FIP virus in the lymphocyte blastogenesis test prior to challenge. Three cats vaccinated once IN and only one cat vaccinated twice subcutaneous showed a similar response.

Two of the five, 2 dose IN vaccinates that showed a lymphocyte blastogenesis response prior to challenge plus a 2 dose IN vaccinate that failed to respond showed a strong blastogenesis response postchallenge. Only lymphocytes from a single cat vaccinated once IN and lymphocytes from no cat vaccinated twice SC responded to FIP virus following challenge.

All six cats vaccinated twice IN were solidly protected against FIP virus challenge. One of six cats (UX6) vaccinated once IN showed blood dyscrasias indicative of FIP but survived. In contrast, two of four non-vaccinated cats and five of six cats vaccinated subcutaneous developed FIP and died. One of two surviving control cats (HI2) showed blood dyscrasias suggesting FIP. Most subcutaneous vaccinated cats developed FIP sooner than non-vaccinated cats.

EXAMPLE 4

Preparation of Combination Vaccine

A combination vaccine consisting of ts-FIP virus combined with calicivirus and feline herpes (rhinotracheitis) virus for intranasal administration can be produced. The combination vaccine may be assembled as follows:

0.5 ml Feline herpes virus ($TCID_{50}$=$10^{7.2}$)

0.50 ml Calicivirus ($TCID_{50}$=$10^{7.9}$)

0.5 ml ts-FIP virus ($TCID_{50}$=$10^{5.5}$)

0.8 ml Stabilizer (NZ-Amine, gelatin or sucrose)

The combination vaccine can be lyophilized for shipment and storage. Prior to use the combination vaccine is rehydrated to 1.0 ml in, for example, water, saline or other diluent Suitable for oral or intranasal adminstration.

EXAMPLE 5

Preparation of a Subunit Vaccine

The immunogenic subunit of ts-FIP virus can be combined with whole virus or subunit components of feline distemper virus, calicivirus, feline herpes virus, feline leukemia virus and chlamydia vaccines and administered parenterally or intranasally. The combination subunit vaccine of this type may be assembled as follows:

0.2 ml of ts-FIP virus ($TCID_{50}=10^{5.5}$)

0.5 ml of feline herpes virus ($TCID_{50}=10^{7.2}$)

0.25 ml of feline distemper virus ($TCID_{50}=10^{6.0}$)

0.25 ml of calicivirus ($TCID_{50}=10^{7.9}$)

0.5 ml of feline leukemia virus (500–3000 μg of gp 70 protein)

0.25 ml of chlamydia ($TCID_{50}=10^{6.5}$)

The concentration of the various feline viruses is that amount known to elicit an effective immune response. Preferably the concentrated virus is prepared in the above recommended volumes in order to have the components in a small volume suitable for administration.

EXAMPLE 6

Two Component Subunit Vaccine

A two component subunit vaccine for parenteral administration can be prepared using the immunogenic subunit of ts-FIP virus combined with the immunogenic feline leukemia virus vaccine. The combination subunit vaccine may be assembled as follows:

0.4 ml ($TCID_{50}=10^{5.5}$) of ts-FIP virus 0.4 ml (25–1000 μg) of feline leukemia virus subunit 0.2 ml adjuvant (aluminum hydroxide, saponin)

EXAMPLE 7

Two Site Administration of Vaccines

The ts-FIP virus vaccine can be administered intranasally (0.5 ml per nostril) at the time of parenteral administration of calicivirus, feline herpes virus, feline distemper virus, feline leukemia virus and chlamydia (feline pneumonitis) combination vaccine. Concentrations of the various components would be as described in Example 4, however, the ts-FIP would be administered intranasally separate from the other virus components.

TABLE 4

Serum IgG Anti FIP Virus Antibody Responses of ts-FIP Virus Vaccinated and Non-Vaccinated Cats in Efficacy Test 1

| Cat No. | Vaccine Titer | ELISA Titer Weeks Postvaccination | | | |
|---|---|---|---|---|---|
| | | 0[a] | 3[b] | 6[c] | 8 |
| KU4 | $10^{5.5}$ $TCID_{50}$/ml | >1.50[d,e] | >1.50 | 1.260 | >1.50 |
| KV4 | | .145[e] | .748 | .806 | 1.183 |
| LZ4 | | .080[e] | .590 | .719 | 1.201 |
| MJ5 | | .040[e] | .557 | .747 | 1.075 |
| MM5 | | .070[e] | .449 | .787 | 1.015 |
| Arithmetic Mean | | .367 | .769 | .864 | 1.195 |

TABLE 4-continued

Serum IgG Anti FIP Virus Antibody Responses of ts-FIP Virus Vaccinated and Non-Vaccinated Cats in Efficacy Test 1

| Cat No. | Vaccine Titer | ELISA Titer Weeks Postvaccination | | | |
|---|---|---|---|---|---|
| | | 0[a] | 3[b] | 6[c] | 8 |
| KT4 | $10^{3.5}$ $TCID_{50}$/ml | .074[e] | .602 | .787 | 1.420 |
| KU2 | | .129[e] | .439 | .650 | 1.179 |
| LC5 | | .095[e] | .505 | .788 | .914 |
| LR7 | | .364[e] | .698 | .676 | 1.024 |
| MG2 | | .095[e] | .676 | .845 | 1.298 |
| Arithmetic Mean | | .151 | .584 | .749 | 1.167 |
| KT3 | None | .483[f] | .881 | .823 | 1.031 |
| KV2 | | .392[f] | .715 | .827 | 1.202 |
| LD4 | | .348[f] | .702 | .842 | .973 |
| LK2 | | .499[f] | .724 | .903 | .925 |
| Arithmetic Mean | | .430 | .755 | .849 | 1.033 |

[a]First vaccination
[b]Second vaccination
[c]Third vaccination
[d]Absorbance Values measured at 405 nm. Values ≧.300 are positive.
[e]Serum collected on day of first vaccination
[f]Serum collected 15 days after first vaccination

TABLE 5

Serum Virus Neutralization Anti-FIP Virus Antibody Titers of ts-FIP Virus Vaccinated and Non-Vaccinated Cats in Efficacy Test 1

| Cat No. | Vaccine Titer | Reciprocal of Virus Neutralization Titer Weeks Postvaccination | | | |
|---|---|---|---|---|---|
| | | 0[a] | 3[b] | 6[c] | 8 |
| KU4 | $10^{5.5}$ $TCID_{50}$/ml | <2[d] | 64 | 192 | NT |
| KV4 | | <2[d] | 24 | 128 | 512 |
| LZ4 | | NT | 16 | 128 | 256 |
| MJ5 | | <2[d] | 192 | 192 | 384 |
| MM5 | | <2d | 16 | 48 | 512 |
| Geometric Mean | | <2 | 38 | 124 | 401 |
| KT4 | $10^{3.5}$ $TCID_{50}$/ml | <2[d] | 96 | 192 | 384 |
| KU2 | | <2[d] | 48 | 96 | 512 |
| LC5 | | NT | 96 | 384 | NT |
| LR7 | | <2[d] | 64 | 96 | 192 |
| MG2 | | <2d | 96 | 256 | 768 |
| Geometric Mean | | <2 | 77 | 177 | 413 |
| KT3 | 0 | <2[e] | <2 | <2 | <2 |
| KV2 | | <2[e] | <2 | <2 | <2 |
| LD4 | | <2[e] | <2 | <2 | <2 |
| LK2 | | <2e | <2 | <2 | <2 |
| Geometric Mean | | <2 | <2 | <2 | <2 |

[a]First vaccination
[b]Second vaccination
[c]Third vaccination
[d]Serum collected on day of first vaccination
[e]Serum collected 15 days after first vaccination

TABLE 6

Serum IgG Anti FIP Virus Antibody Response of ts-FIP Virus Vaccinated and Non-Vaccinated Cats in Efficacy Test 2

| Cat No. | No of Times Vaccinated IN | ELISA Titer Weeks Postvaccination | | | | | |
|---|---|---|---|---|---|---|---|
| | | −1[a] | 3[b] | 3[c] | 3[d] | 12 | 18 |
| SD1 | 3 | .110[e] | .348 | .683 | .633 | 1.078 | 1.249 |
| SL2 | | .135 | .346 | .669 | .482 | 1.089 | 1.264 |

TABLE 6-continued

Serum IgG Anti FIP Virus Antibody Response of ts-FIP Virus Vaccinated and Non-Vaccinated Cats in Efficacy Test 2

| Cat No. | No of Times Vaccinated IN | ELISA Titer Weeks Postvaccination −1[a] | 3[b] | 3[c] | 3[d] | 12 | 18 |
|---|---|---|---|---|---|---|---|
| SN1 | | .086 | .483 | .812 | .776 | 1.094 | 1.397 |
| SO2 | | .196 | .321 | .573 | .620 | 1.095 | 1.094 |
| ST2 | | .164 | .268 | .609 | .532 | 1.275 | 1.229 |
| SY3 | | .147 | .532 | 1.013 | .768 | 1.232 | 1.424 |
| Arithmetic Mean | | .140 | .383 | .726 | .635 | 1.144 | 1.273 |
| RY5 | 2[f] | .106 | .383 | .740 | .725 | .987 | 1.003 |
| SI2 | | .282 | .299 | .718 | .738 | 1.130 | 1.054 |
| SY1 | | .106 | .383 | .868 | .792 | 1.271 | 1.421 |
| Arithmetic Mean | | .165 | .355 | .775 | .752 | 1.129 | 1.162 |
| RZ3 | 0 | .123 | .052 | .063 | .073 | .589 | Dead |
| SH4 | | .074 | .030 | .047 | .049 | .417 | Dead |
| SL5 | | .155 | .051 | .074 | .040 | .291 | 0.609 |
| Arithmetic Mean | | .117 | .044 | .061 | .054 | .432 | 0.609 |

[a]First vaccination
[b]Second vaccination
[c]Third vaccination
[d]Challenged 4 weeks post third vaccination
[e]Absorbance Values measured at 405 nm. Values ≧.300 are positive.
[f]Vaccinated a third time orally.

TABLE 7

Serum Virus Neutralization Anti-FIP Virus Antibody Titers of ts-FIP Virus Vaccinated and Non-Vaccinated Cats in Efficacy Test 2

| Cat No. | No of Times Vaccinated IN | Reciprocal of Virus Neutralization Titer Weeks Postvaccination −1[a] | 3[b] | 6[c] | 9[d] | 12 | 18 |
|---|---|---|---|---|---|---|---|
| SD1 | 1 | 0 | 64 | 384 | NT | 192 | 96 |
| SL2 | | 0 | 96 | 1024 | 240 | 7200 | 9600 |
| SN1 | | 0 | 48 | 256 | 360 | 4800 | 9600 |
| SO2 | | 0 | 48 | 192 | NT | 900 | 192 |
| ST2 | | 0 | 192 | 768 | 120 | NT | 64 |
| SY3 | | 0 | 48 | 768 | 360 | 7200 | 7200 |
| Geometric Mean | | 0 | 71 | 474 | 247 | 2122 | 960 |
| RY5 | 2[e] | 0 | 48 | 192 | NT | 192 | 600 |
| SI2 | | 0 | 48 | 256 | 120 | 128 | 64 |
| SY1 | | 0 | 96 | 1024 | 360 | 900 | 9600 |
| Geometric Mean | | 0 | 60 | 369 | 208 | 281 | 717 |
| RZ3 | 0 | 0 | 0 | 8 | 0 | 900 | Dead |
| SH4 | | 0 | 0 | 1 | 0 | 600 | Dead |
| SL5 | | 0 | 0 | 1 | 0 | 2 | 3 |
| Geometric Mean | | 0 | 0 | 2 | 0 | 81 | 3 |

[a]First vaccination
[b]Second vaccination
[c]Third vaccination
[d]Challenged 4 weeks post third vaccination
[e]Vaccinated a third time orally.

TABLE 8

Serum IgG Anti FIP Virus Antibody Response of Intranasal and Subcutaneous ts-FIP Virus Vaccinated and Non-Vaccinated Cats in Efficacy Test 3

| Cat No. | Route/No. of Vaccinations | ELISA Titer Weeks Postvaccination 0[a] | 3[b] | 8[c] | 11 | 14 | 16 |
|---|---|---|---|---|---|---|---|
| SU4 | IN/1 | 0.028[d] | 0.012 | 0.399 | 0.476 | 0.334 | 0.474 |
| TR3 | | 0.017 | 0.007 | 0.603 | 0.552 | 0.428 | 0.697 |
| TT2 | | 0.018 | 0.011 | 0.592 | 1.153 | 0.745 | 1.321 |
| UN3 | | 0.012 | 0.010 | 0.674 | 0.948 | 0.673 | 1.400 |
| UO4 | | 0.064 | 0.021 | 0.329 | 0.414 | 0.397 | 0.269 |
| UX6 | | 0.035 | 0.020 | 0.683 | 1.116 | 0.856 | 1.475 |
| Arith. Mean | | 0.029 | 0.014 | 0.547 | 0.776 | 0.574 | 0.939 |
| OH2 | IN/2 | 0.016 | 0.351 | 0.858 | 0.537 | 0.443 | 0.878 |
| PQ4 | | 0.104 | 0.095 | 0.578 | 0.682 | 0.610 | 0.704 |
| QK4 | | 0.013 | 0.191 | 0.660 | 0.502 | 0.498 | 0.727 |
| UE1 | | 0.029 | 0.223 | 0.881 | 1.193 | 0.885 | 1.543 |
| US1 | | 0.018 | 0.151 | 0.796 | 1.212 | 0.934 | 1.629 |
| US2 | | 0.016 | 0.176 | 0.773 | 0.731 | 0.514 | 0.886 |
| Arith. Mean | | 0.033 | 0.198 | 0.758 | 0.809 | 0.647 | 1.061 |
| QG2 | SC/2 | 0.030 | 0.021 | 0.229 | Dead | Dead | Dead |
| QJ1 | | 0.125 | 0.142 | 0.235 | 0.828 | Dead | Dead |
| QY3 | | 0.189 | 0.108 | 0.603 | 1.034 | Dead | Dead |
| RG3 | | 0.017 | 0.150 | 0.516 | 0.981 | 1.37 | Dead |
| TU4 | | 0.031 | 0.042 | 0.235 | 0.495 | 0.135 | 0.121 |
| UG1 | | 0.018 | 0.243 | 0.507 | 1.388 | Dead | Dead |
| Arith. Mean | | 0.068 | 0.118 | 0.388 | 0.945 | 0.752 | 0.121 |
| HH5 | Control | NT[e] | 0.041 | 0.042 | 0.403 | Dead | Dead |
| HJ4 | | NT | 0.015 | 0.062 | 0.561 | NT | 1.205 |
| HG2 | | NT | 0.030 | 0.059 | 0.744 | 0.743 | Dead |
| HI2 | | NT | 0.007 | 0.048 | 0.298 | 0.514 | 1.225 |
| Arith. Mean | | | 0.023 | 0.053 | 0.501 | 0.629 | 1.215 |

[a]First Vaccination of cats receiving 2 doses
[b]Second vaccination of cats receiving 2 doses and first vaccination of cats receiving one dose
[c]Titers one week before challenge
[d]Absorbance values measured at 405 nm. Values ≧0.300 are positive.
[e]Not Tested.

TABLE 9

Serum Virus Neutralization Anti-FIP Virus Antibody Titers of ts-FIP Virus Intranasal and Subcutaneous Vaccinated and Nonvaccinated Cats in Efficacy Test 3

| Cat No. | Route/No. of Vaccinations | Reciprocal of Virus Neutralization Titer Weeks Postvaccination 0[a] | 3[b] | 8[c] | 11 | 14 | 16 |
|---|---|---|---|---|---|---|---|
| SU4 | IN/1 | <4 | <8 | 64 | 30 | 20 | 20 |
| TR3 | | <2 | <8 | 256 | 120 | 120 | 40 |
| TT2 | | <2 | <8 | 96 | 1920 | 640 | 480 |
| UN3 | | <2 | <8 | 512 | 320 | 3840 | 1280 |
| UO4 | | 3 | 8 | 48 | 40 | 30 | 20 |
| UX6 | | 4 | 8 | 192 | 960 | 960 | 1920 |
| Geometric Mean | | <2 | <8 | 140 | 210 | 235 | 163 |
| OH2 | IN/2 | <2 | 48 | 256 | 120 | 60 | 80 |
| PQ4 | | <2 | 96 | 512 | 120 | 60 | 60 |
| QK4 | | <2 | 96 | 192 | 80 | 40 | 120 |
| UE1 | | <2 | 128 | 768 | 1920 | 2560 | 2560 |
| US1 | | <2 | 96 | 512 | 160 | 640 | 960 |
| US2 | | <2 | 64 | 512 | 120 | 240 | 80 |
| Geometric Mean | | <2 | 84 | 414 | 187 | 196 | 220 |
| QG2 | SC | <2 | <8 | 8 | Dead | Dead | Dead |
| QJ1 | | <2 | <8 | <8 | 1280 | Dead | Dead |
| QY3 | | <2 | <8 | 128 | 640 | Dead | Dead |
| RG3 | | 24 | 8 | 64 | 1920 | Dead | Dead |
| TU4 | | <2 | <8 | 12 | <20 | 20 | <20 |
| UG1 | | <2 | 12 | 32 | 640 | Dead | Dead |

TABLE 9-continued

Serum Virus Neutralization Anti-FIP Virus Antibody Titers of ts-FIP Virus Intranasal and Subcutaneous Vaccinated and Nonvaccinated Cats in Efficacy Test 3

| | Route/No. of | Reciprocal of Virus Neutralization Titer Weeks Postvaccination | | | | | |
|---|---|---|---|---|---|---|---|
| Cat No. | Vaccinations | 0[a] | 3[b] | 8[c] | 11 | 14 | 16 |
| Geometric Mean | | <2 | <8 | 24 | 399 | 20 | <20 |
| HH5 | Control | NT[d] | NT | <2 | 120 | Dead | Dead |
| HJ4 | | NT | NT | <2 | 120 | 480 | 480 |
| HG2 | | NT | NT | <2 | 960 | Dead | Dead |
| HI2 | | NT | NT | <2 | 240 | 3480 | 640 |
| Geometric Mean | | | | <2 | 240 | 1292 | 554 |

[a]First Vaccination of cats receiving 2 doses
[b]Second vaccination of cats receiving 2 doses and first vaccination of cats receiving one dose
[c]Titers one week before challenge
[d]Not Tested.

TABLE 10

Serum IgG Anti FIPV ELISA Antibody Response of Intranasal HPA-FIPV and TS-FIPV Vaccinated and Nonvaccinated Cats

| | Vaccine | ELISA Value Days Postvaccination | | | | |
|---|---|---|---|---|---|---|
| Cat No. | ($TCID_{50}$) | -14[a] | 21[b] | 42[c] | 70 | 98 |
| CP4 | TS-FIPV | 0.04[d] | 0.20 | 0.51 | 0.86 | 0.86 |
| DV3 | (4.7) | 0.02 | 0.39 | 0.53 | 1.16 | 1.27 |
| EA1 | | 0.03 | 0.48 | 0.67 | 1.16 | 1.21 |
| EA2 | | 0.04 | 0.39 | 0.70 | 1.27 | 1.21 |
| ED3 | | 0.02 | 0.20 | 0.39 | 0.96 | 1.06 |
| EI1 | | 0.01 | 0.36 | 0.46 | 0.98 | 1.02 |
| Arith. Mean | | 0.02 | 0.33 | 0.54 | 1.06 | 1.10 |
| CQ4 | TS-FIPV | 0.04 | 0.44 | 0.68 | Dead | Dead |
| DW2 | (5.7) | 0.03 | 0.44 | 0.56 | 1.25 | Dead |
| DZ1 | | 0.02 | 0.45 | 0.45 | 0.95 | 0.89 |
| EC2 | | 0.02 | 0.51 | 0.99 | 1.31 | 1.22 |
| EF4 | | 0.02 | 0.59 | 0.65 | Dead | Dead |
| LM1 | | 0.01 | 0.55 | 0.63 | 1.09 | 1.10 |
| MD3 | | 0.06 | 0.35 | 0.70 | 1.13 | 1.02 |
| MD6 | | 0.05 | 0.40 | 0.59 | 1.28 | 1.34 |
| MH3 | | 0.05 | 0.44 | 0.58 | 1.19 | 1.34 |
| MH4 | | 0.04 | 0.53 | 0.59 | 1.05 | 1.20 |
| MH6 | | 0.04 | 0.28 | 0.40 | 1.16 | 1.68 |
| MJ5 | | 0.03 | 0.56 | 0.64 | 1.25 | 1.28 |
| MN2 | | 0.04 | 0.38 | 0.79 | 1.16 | 1.53 |
| MS3 | | 0.04 | 0.37 | 0.74 | 1.18 | 1.20 |
| Arith. Mean | | 0.03 | 0.44 | 0.64 | 1.16 | 1.25 |
| MC1 | HPA-FIPV | 0.14 | 0.75 | 1.09 | 1.35 | 1.38 |
| MD5 | (6.4) | 0.17 | 0.50 | 0.83 | Dead | Dead |
| ML6 | | 0.06 | 0.80 | 0.85 | 1.32 | 1.65 |
| MS2 | | 0.04 | 0.79 | 0.93 | 1.32 | 1.23 |
| Arith. Mean | | 0.11 | 0.71 | 0.93 | 1.33 | 1.42 |
| CS1[e] | Control | 0.04 | 0.17 | 0.11 | Dead | Dead |
| MH2[e] | | 0.04 | 0.09 | 0.40 | 1.51 | Dead |
| CP3 | | 0.04 | 0.20 | 0.09 | Dead | Dead |
| CZ1 | | 0.05 | 0.14 | 0.21 | 1.56 | Dead |
| DU5 | | 0.04 | 0.04 | 0.08 | Dead | Dead |
| EB2 | | 0.02 | 0.23 | 0.14 | 1.24 | Dead |
| EI2 | | 0.28 | 0.22 | 0.22 | 1.34 | 1.27 |
| EN1 | | 0.00 | 0.09 | 0.06 | Dead | Dead |
| KF1 | | 0.03 | 0.06 | 0.07 | Dead | Dead |
| MC2 | | 0.04 | 0.06 | 0.07 | Dead | Dead |
| MK5 | | 0.06 | 0.11 | 0.07 | 1.13 | Dead |
| MK6 | | 0.04 | 0.05 | 0.07 | 1.01 | 1.34 |
| Arith. Mean | | 0.06 | 0.12 | 0.10 | 1.30 | 1.30 |

TABLE 10-continued

Serum IgG Anti FIPV ELISA Antibody Response of Intranasal HPA-FIPV and TS-FIPV Vaccinated and Nonvaccinated Cats

| | Vaccine | ELISA Value Days Postvaccination | | | | |
|---|---|---|---|---|---|---|
| Cat No. | ($TCID_{50}$) | -14[a] | 21[b] | 42[c] | 70 | 98 |

[a]First vaccination of cats — Day 0
[b]Second vaccination of cats — Day 21
[c]Challenge — Day 42
[d]Absorbance values measured at 410 nm. Values of ≧0.300 are positive.
[e]Vaccine contact controls.

TABLE 11

Serum IgA Anti FIPV ELISA Antibody Response of Intranasal HPA-FIPV and TS-FIPV Vaccinated and Nonvaccinated Cats

| | Vaccine | ELISA Value Days Postvaccination | | | | |
|---|---|---|---|---|---|---|
| Cat No. | ($TCID_{50}$) | -14[a] | 21[b] | 42[c] | 70 | 98 |
| CP4 | TS-FIPV | 0.03[d] | 0.00 | 0.02 | 0.16 | 0.14 |
| DV3 | (4.7) | 0.01 | 0.00 | 0.11 | 0.32 | 0.18 |
| EA1 | | 0.22 | 0.21 | 0.65 | 0.42 | 0.40 |
| EA2 | | 0.01 | 0.01 | 0.21 | 0.41 | 0.29 |
| ED3 | | 0.12 | 0.02 | 0.42 | 0.26 | 0.31 |
| EI1 | | 0.20 | 0.07 | 0.11 | 0.11 | 0.26 |
| Arith. Mean | | 0.10 | 0.05 | 0.29 | 0.28 | 0.26 |
| CQ4 | TS-FIPV | 0.09 | 0.06 | 0.13 | Dead | Dead |
| DW2 | (5.7) | 0.03 | 0.03 | 0.09 | 0.32 | 0.32 |
| DZ1 | | 0.08 | 0.06 | 0.11 | 0.15 | 0.27 |
| EC2 | | 0.20 | 0.05 | 0.16 | 0.26 | 0.32 |
| EF4 | | 0.01 | 0.01 | 0.08 | Dead | Dead |
| LM1 | | 0.06 | 0.04 | 0.08 | 0.13 | 0.28 |
| MD3 | | 0.07 | 0.08 | 0.18 | 0.31 | 0.46 |
| MD6 | | 0.06 | 0.03 | 0.08 | 0.18 | 0.17 |
| MH3 | | 0.27 | 0.23 | 0.29 | 0.34 | 0.26 |
| MH4 | | 0.17 | 0.08 | 0.12 | 0.26 | 0.27 |
| MH6 | | 0.18 | 0.15 | 0.22 | 0.29 | 0.35 |
| MJ5 | | 0.17 | 0.09 | 0.14 | 0.23 | 0.27 |
| MN2 | | 0.17 | 0.15 | 0.09 | 0.18 | 0.22 |
| MS3 | | 0.11 | 0.09 | 0.15 | 0.17 | 0.18 |
| Arith. Mean | | 0.12 | 0.08 | 0.14 | 0.24 | 0.28 |
| MC1 | HPA-FIPV | 0.05 | 0.12 | 0.14 | 0.49 | 0.33 |
| MD5 | (6.4) | 0.09 | 0.27 | 0.34 | Dead | Dead |
| ML6 | | 0.09 | 0.13 | 0.17 | 0.39 | 0.35 |
| MS2 | | 0.02 | 0.11 | 0.13 | 0.28 | 0.15 |
| Arith. Mean | | 0.06 | 0.15 | 0.19 | 0.39 | 0.28 |
| CS1[e] | Control | 0.09 | 0.03 | 0.13 | Dead | Dead |
| MH2[e] | | 0.08 | 0.02 | 0.16 | 0.37 | Dead |
| CP3 | | 0.00 | 0.00 | 0.10 | Dead | Dead |
| CZ1 | | 0.10 | 0.06 | 0.19 | 0.61 | Dead |
| DU5 | | 0.03 | 0.03 | 0.07 | Dead | Dead |
| EB2 | | 0.20 | 0.08 | 0.24 | 0.16 | Dead |
| EI2 | | 0.08 | 0.00 | 0.14 | 0.38 | 0.39 |
| EN1 | | 0.29 | 0.04 | 0.28 | Dead | Dead |
| KF1 | | 0.10 | 0.04 | 0.17 | Dead | Dead |
| MC2 | | 0.00 | 0.01 | 0.07 | Dead | Dead |
| MK5 | | 0.06 | 0.01 | 0.16 | 0.40 | Dead |
| MK6 | | 0.02 | 0.00 | 0.06 | 0.16 | 0.31 |
| Arith. Mean | | 0.09 | 0.02 | 0.15 | 0.35 | 0.35 |

[a]First vaccination of cats — Day 0
[b]Second vaccination of cats — Day 21
[c]Challenge — Day 44
[d]Absorbance values measured at 410 nm.
[e]Vaccine contact controls.

TABLE 12

Serum Virus Neutralization Anti-FIPV Antibody Titers of HPA-FIPV and TS-FIPV Vaccinated and Non-vaccinated Cats

| | Vaccine | Reciprocal of Virus Neutralization Titer Days Postvaccination | | | | |
|---|---|---|---|---|---|---|
| Cat No. | ($TCID_{50}$) | -14[a] | 21[b] | 42[c] | 70 | 98 |
| CP4 | TS-FIPV | <2 | <20 | 20 | 48 | 24 |
| DV3 | (4.7) | <2 | 120 | 160 | 192 | 96 |
| EA1 | | <2 | 40 | 80 | 64 | 192 |
| EA2 | | <2 | 60 | 160 | 1024 | 1536 |
| ED3 | | <2 | <20 | 40 | 96 | 64 |
| EI1 | | <2 | <20 | 60 | 48 | 64 |
| Geometric Mean | | 1 | 36 | 73 | 119 | 119 |
| CQ4 | TS-FIPV | <2 | 80 | 160 | Dead | Dead |
| DW2 | (5.7) | <2 | 60 | 120 | 3072 | Dead |
| DZ1 | | <2 | 40 | 80 | 48 | 24 |
| EC2 | | <2 | <20 | 120 | 384 | 384 |
| EF4 | | <2 | 30 | 120 | 4096 | Dead |
| LM1 | | <2 | 30 | 60 | 96 | 48 |
| MD3 | | <2 | <20 | 120 | 96 | 32 |
| MD6 | | <2 | 30 | 240 | 2048 | 3071 |
| MH3 | | <2 | 60 | 30 | 4096 | 512 |
| MH4 | | <2 | 30 | 120 | 384 | 96 |
| MH6 | | <2 | <20 | 20 | 8192 | 12288 |
| MJ5 | | <2 | 30 | 120 | 192 | 64 |
| MN2 | | <2 | 40 | 80 | 96 | 192 |
| MS3 | | <2 | 20 | 129 | 96 | 96 |
| Geometric Mean | | 1 | 28 | 92 | 492 | 208 |
| MC1 | HPA-FIPV | <2 | 96 | 384 | 256 | 384 |
| MD5 | (6.4) | <2 | 256 | 256 | Dead | Dead |
| ML6 | | <2 | 128 | 1536 | 1024 | 4096 |
| MS2 | | <2 | 256 | 1024 | 1024 | 768 |
| Geometric Mean | | 1 | 168 | 627 | 645 | 1065 |
| CS1[d] | Control | <2 | <2 | <2 | Dead | Dead |
| MH2[d] | | <2 | <2 | 30 | 8192 | Dead |
| CP3 | | <2 | <2 | <2 | Dead | Dead |
| CZ1 | | <2 | <2 | <2 | 1024 | Dead |
| DU5 | | <2 | <2 | <2 | Dead | Dead |
| EB2 | | <2 | <2 | <2 | 3072 | Dead |
| EI2 | | <2 | <2 | <2 | 4096 | 4096 |
| EN1 | | <2 | <2 | <2 | Dead | Dead |
| KF1 | | <2 | <2 | <2 | Dead | Dead |
| MC2 | | <2 | <2 | <2 | Dead | Dead |
| MK5 | | <2 | <2 | <2 | 1536 | Dead |
| MK6 | | <2 | <2 | <2 | 2048 | 4096 |
| Geometric Mean | | 1 | 1 | 1 | 2631 | 4096 |

[a]First vaccination of cats — Day 0
[b]Second vaccination of cats — Day 21
[c]Challenge — Day 44
[d]Vaccine contact controls.

EXAMPLE 8

Intranasal Administration of High Passage Attenuated FIP Virus

This Example illustrates the efficacy of a high passage attenuated FIP virus vaccine administered intranasally.

To prepare the high passage attenuated FIP Virus (HPA-FIPV) FIP virus was passaged 100 times Feline kidney (FK) cells. From passage 1 to passage 61, the FIP virus (FIP Virus-DF2) was propagated at 39 C, and from passage 62 to passage 100, the virus was propagated at 31 C.

The vaccine was prepared by infection of a 6 day old confluent FK monolayer grown in an 850 $cm^2$ roller bottle with the 100th passage of the HPA-FIPV. The viral fluids were inoculated at a muliplicity of infection of approximately 0.1 (i.e., 1 virus per 10 cells) using 100 mls of scrim-free Minimum Essential Medium (MEM) as the maintenance medium. The roller bottle was incubated at 31 C for 48 hours after which, the viral fluids were harvested and stored at −70 C.

Titrations of the viral fluids were done by addition of each 10 fold serial dilution from $10^{-1}$ to $10^{-8}$ to 5 replicate wells of a 96-well plate with 2 day old confluent FK monolayers. Duplicate plates were incubated at 31 C and 39 C for 4 days before the Reed-Muench end points (Amer. J. Hygiene 27:93 (1938)) were determined.

Four SPF CATS (Liberty Labs, Liberty, N.J.), approximately 1 year of age, were vaccinated twice, intranasally, 3 weeks apart with 1 ml of the HPA-FIPV, passage 101, in stock fluids diluted 1:10 using Basal Medium Eagle (BE). The cats were vaccinated with the HPA-FIPV at the time that twenty SPF cats from Liberty Laboratories were vaccinated twice with TS-FIPV.

Three weeks after the second vaccination the cats were challenged orally with 1 ml of virulent FIPV (DF2 passage 10) diluted 1:600 in BME. Two TS-FIPV vaccine contact controls and 10 naive controls were challenged along with the 4 HPA-FIPV vaccinates and 20 TS-FIPV vaccinates.

The HPA-FIPV vaccinates showed an immune response to FIPV after vaccination as measured by IgG ELISA, IgA ELISA, and virus neutralization. (See Tables 10, 11 and 12).

Three of four cats (75%) vaccinated with HPA-FIPV and 17 of 20 cats (85%) vaccinated with the TS-FIPV vaccine survived a rigorous FIPV challenge which killed 10 of 12 (83%) nonvaccinated controls.

The Example demonstrates that the intranasal route of administration provides a surprisingly high degree of protection against FIP infection. Intranasal administration either with HPA-FIPV or TS-FIPV protected cats against a rigorous FIPV challenge.

The above description and examples fully disclose the invention including preferred embodiments thereof. Modifications of the methods described that are obvious to those of skill in the art of vaccine production for use in small animals are intended to be within the scope of the following claims.

What is claimed is:

1. A method for protecting cats against infection by feline infectious peritonitis virus (FIP), which comprises intranasally administering an effective amount of an FIP Virus vaccine, said virus vaccine comprising a temperature-sensitive, attenuated FIP virus having a titer following propagation at 31° C. which is at least about $1\times10^2$ to about $1\times10^5$ $TCID_{50}$ greater than at 39° C.

2. The method of claim 1 wherein the virus is attenuated by multiple passage in cell culture and is made temperature sensitive by exposure to ultraviolet irradiation.

3. The method of claim 1, wherein the virus exhibits a titer following propagation a 31° C. which is at least about $1\times10^5$ $TCID_{50}$ greater than at 39° C.

4. A device for immunizing cats against FIP infection, comprising a dropper or a spray bottle further comprising an FIP Virus vaccine, said virus vaccine comprising a temperature-sensitive, attenuated FIP Virus having a titer following propagation at 31° C. which is at least about $1\times10^2$ to about $1\times10^5$ $TCID_{50}$ greater than at 39° C.

5. A feline infectious peritonitis (FIP) vaccine for oral or intranasal administration which, following administration, induces immunity against infection by FIP virus in cats without serious side effects, which comprises an effective amount of a temperature sensitive (ts), attenuated FIP virus, said virus having a titer following propagation at 31° C. which is at least about $1\times10^2$ to about $1\times10^5$ $TCID_{50}$ greater than at 39° C.

6. The vaccine of claim 5 wherein the temperature sensitive FIP virus is attenuated by the serial passage in cat cells of virulent FIP virus isolated from the tissue or organs of infected cats.

7. The vaccine of claim 6 wherein the temperature sensitive FIP virus is attenuated by at least 60 successive passages in cat kidney cells.

8. The vaccine of claim 6 wherein the attenuated FIP virus is made temperature sensitive by exposure of the FIP virus to a mutagenic agent.

9. The vaccine of claim 7 wherein the attenuated FIP virus is made temperature sensitive by exposure of the FIP virus to a mutagenic agent.

10. The vaccine of claim 8 wherein the mutagenic agent is ultraviolet light.

11. The vaccine of claim 9 wherein the mutagenic agent is ultraviolet light.

12. The vaccine of claim 10 wherein the FIP virus is exposed to ultraviolet light for 3 to 5 minutes.

13. The vaccine of claim 11 wherein the FIP virus is exposed to ultraviolet light for 3 to 5 minutes.

14. The vaccine of claim 8 wherein the attenuated FIP virus shows a virus titer following propagation at 31° C. which is at least about $1\times10^5$ $TCID_{50}$ greater than at 39° C.

15. The vaccine of claim 9 wherein the attenuated FIP virus shows a virus titer following propagation at 31° C. which is at least about $1\times10^5$ $TCID_{50}$ greater than at 39° C.

16. The vaccine of claim 5, in which the temperature-sensitive, attenuated FIP virus is present in a concentration range of from $10^2$ to $10^7$ $TCID_{50}$ per dose.

17. A method of preparing a vaccine against FIP for oral or intranasal administration, which vaccine is capable of inducing immunity in cats against infection by FIP virus without serious side effects, comprising:

a) culturing a virulent strain of FIP virus;

b) attenuating the FIP virus of step (a) by high passage in susceptible cells;

c) exposing the attenuated FIP virus of step (b) to a mutagenic agent to produce mutated, attenuated FIP viruses;

d) selectively culturing from the mutated, attenuated FIP viruses of step (c) a temperature-sensitive, attenuated FIP virus having a titer following propagation at 31° C. which is at least about $1\times10^2$ to about $1\times10^5$ $TCID_{50}$ greater than at 39° C.; and e) collecting the temperature-sensitive, attenuated FIP virus of step (d).

18. The method according to claim 17 wherein the FIP virus is isolated from the tissue or organs of a feline infected with virulent FIP prior to attenuation.

19. The method according to claim 17, wherein the FIP virus is attenuated by at least 60 successive passages in feline kidney cells.

20. The method according to claim 17 wherein the FIP virus is made temperature sensitive by exposing the high passage FIP virus to ultraviolet light for 3 to 5 minutes.

21. A vaccine dosage unit for inducing immunity in cats against infection by FIP virus, which comprises 0.5 to 1.5 ml of a liquid, suitable for intranasal or oral administration to a feline, said liquid containing $10^2$ to $10^7$ $TCID_{50}$ of a temperature sensitive, attenuated FIP virus having a titer following propagation at 31° C. which is at least about $1\times10^2$ to about $1\times10^5$ $TCID_{50}$ greater than at 39° C.

22. A kit comprising first and second components, the first component being a container further comprising an FIP vaccine in lyophilized form, said vaccine comprising an effective amount of a temperature-sensitive, attenuated FIP virus, said Virus having a titer following propagation at 31° C. which is at least about $1\times10^2$ to about $1\times10^5$ $TCID_{50}$ greater than at 39° C., and the second component being a dropper suitable for intranasal administration comprising a diluent for reconstitution of the lyophilized vaccine.

* * * * *